US00PP09003P

United States Patent [19]

Stravers

[11] Patent Number: Plant 9,003

[45] Date of Patent: Dec. 6, 1994

[54] *GERBERA JAMESONII* PLANT NAMED TERHELENA

[75] Inventor: Lambertus J. M. Stravers, Kudelstaart, Netherlands

[73] Assignee: Terra Nigra B.V., De Kwakel, Netherlands

[21] Appl. No.: 172,261

[22] Filed: Dec. 23, 1993

[51] Int. Cl.[5] ..... A01H 5/00

[52] U.S. Cl. ..... Plt./68.1

[58] Field of Search ..... Plt. 68.1

*Primary Examiner*—James R. Feyrer

[57] ABSTRACT

A new and distinct cultivar of Gerbera plant named 'Terhelena', as illustrated and described, characterized by its semi-double type, a very distinct red purple ray floret which is a solid red-purple color throughout, a green disc floret, the outermost florets of which display white stigmas and the middle flowers of which show yellow-orange anthers, red perianth lobe color and 120 mm overall flower diameter.

1 Drawing Sheet

BACKGROUND OF THE INVENTION

The present invention comprises a new and distinct cultivar of *Gerbera Jamesonii,* referred to by the cultivar name 'Terhelena'. 'Terhelena' was originated from a hybridization program in De Kwakel, the Netherlands in 1989. The female parent was '83.151', and the male parent was '81D138'. The female parent '83.151' differs from 'Terhelena' by its singleness, its pink color, and its smaller flowerdiameter (approx. 110 mm). '83.151' has not been patented in the United States. Moreover, it was not available to others outside the company. The male parent '81D138' differs from 'Terhelena' by its light red color, its high productivity, its good vaselife and smaller flowerdiameter (aprox. 100 mm). '81D138' has not been patented in the United States. Moreover, it was not available to others outside the company. The new cultivar was selected by me from the progeny of the stated parentage on or about November 1989. The first asexual reproduction of 'Terhelena' was accomplished when vegitative cuttings for tissue culture initiation were taken on December 1989 in De Kwakel, The Netherlands. The new cultivar is presently being propagated by cuttings and tissue culture. Horticultural examination of selected units initiated December 1989 has demonstrated that the combination of characteristics as herein disclosed for 'Terhelena' are firmly fixed and are retained through successive generations of asexual reproduction. The following observations, measurements and comparisons describe plants grown in De Kwakel, The Netherlands, under greenhouse conditions which closely approximate those generally used in commercial practice. The following traits have been repeatedly observed and are determined to be basic characteristics of 'Terhelena', which in combination distinguish this Gerbera from its parents and all other varieties of which I am aware:

1. Type: Semi-double.
2. Color of floret: Distinctive purple-red.
3. Color of disc floret: Green.
4. Color of perianthy lobe: Purple-red.
5. Diameter of flower head: Large 120 mm.

Of the many commercial cultivars known to me, there is no cultivar similar in comparison to 'Terhelena'.

BRIEF DESCRIPTION OF THE FIGURE OF THE DRAWING

The accompanying photographic drawing shows typical inflorescence characteristics nearly true as possible. In the following description, color references are made to the Royal Horticultural Society Color Chart (RHS). The color values were determined at approximately 10:30 a.m. on 15-08-91 under natural light at De Kwakel.

BOTANICAL DESCRIPTION OF THE PLANT

Botanical: *Gerbera jamesonii* cv 'Terhelena'.

INFLORESCENCE

A. Capitulum:
- *Form.*—Flat shaped.
- *Type.*—Semi-double.
- *Diameter across face.*—120 mm.

B. Corolla of ray florets:
- *Color (general tonality from a distance of* 3 *meters)*-.—Purple-red.
- *Color (topside).*—Purple-red RHS 53C.
- *Color (bottom).*—Red RHS 55B.

C. Corolla of disc florets:
- *Color (mature).*—Yellow-green RHS 145A.
- *Color (immature).*—Yellow-green RHS 145A.

D. Reproductive organs:
- *Stigma.*—White RHS 155D.
- *Anthers.*—Yellow-orange RHS 21B.
- *Pappus.*—Yellow RHS 2C.

PLANT

A. General appearance:
- *Height.*—40 cm.

B. Foliage:
- *Color (abaxial).*—Green RHS 137A.
- *Color (adaxial).*—Green RHS 137A.
- *Shape.*—The angle of apex: Right angle. The shape of apex: Pointed. The margin of lobes: Crenate.

C. Disease resistance: No special disease resistance.

OTHER CHARACTERISTICS

The following traits have been repeatedly observed and are determined to be basic characteristics of 'Terhelena', which in combination distinguish this Gerbera as a new and distinct cultivar.

Leaf blade:

*Length.*—Long.

*Width.*—Medium.

*Thickness.*—Medium.

*Blistering.*—Medium.

*Pubescence.*—On upper side (midrib excluded): Medium.

*Depth of cuts or incisions in leaf.*—Basal part: Deep. Central part: Deep. Distal part: Shallow.

*Color.*—Upper side of the leaf blade is green (RHS 137A).

*Glossiness on upper side.*—Medium.

*Angle of apex.*—Right angle.

*Shape of apex.*—Pointed.

*Margin of lobes.*—Crenate.

*Extensions of margin.*—Medium.

*Petiole length.*—Long; 15 cm.

*Flowering season in the greenhouse.*—Year round, with less productivity during the winter period.

*Productivity in soil.*—Approximately 22 flowers per plant, per year.

*Productivity in rockwool.*—Approximately 26 flowers per plant per year.

*Petiole anthocyanin coloration.*—Medium.

Peduncle:

*Length.*—Long (approx. 70 cm).

*Cross section.*—Round.

*Tendency to fasciation.*—Absent.

*Thickness.*—Medium.

*Strength.*—Medium.

*Pubescence.*—Medium.

*Color.*—Medium green.

*Anthocyanin coloration.*—At base: Medium. At top: Absent.

*Involucral bracts.*—Present.

Flower head:

*Type.*—Semi-double.

*Diameter.*—Large (approx. 120 mm).

*Involucre.*—Height: Medium (25 mm). Diameter: Medium (45–50 mm). Number of bracts: Medium (approx. 60). Longitudinal axis of bracts of inner rows: Straight. Anthocyanin: Absent. Pubescence: Medium.

*Phyllaries.*—Number: Approximately 50. Size: Length: approximately 1.5–2 cm. Width: approximately 1.5–2 mm.

*Ray florets.*—Number: Medium (approx. 55). Shape: Obovate. Longitudinal axis outer row: Reflexing. Longitudinal axis inner row: Straight.

*Outer ray florets.*—Cross section: Flat. Length: Medium (50 mm). Width: Medium. Longitudinal folding: Medium. Angle of apex: Right angle. Shape of apex: Rounded. Incisions of apex: Present. Number: one. Depth: medium. Length of free petals: Long. Color distribution on inner side: Uniform. Edge of different color: Absent. Striation: Absent. Claw spot: Present.

Disc florets:

*Diameter.*—Medium (45–50 mm).

*Main color perianth lobes.*—Female flowers: red (RHS 55B). Male flowers: red-purple (RHS 61B).

Reproductive parts:

*Stigma.*—Main color white (RHS 155D).

*Anthers.*—Main color yellow-orange (RHS 21B).

*Pappus.*—Main color yellow (RHS 2C).

*Fertility.*—Almost sterile; hardly any pollen developed, so also seedsetting is very difficult.

I claim:

1. A new and distinct cultivar of Gerbera plant named 'Terhelena', as illustrated and described, characterized by its semi-double type, a very distinct red purple ray floret which is a solid color throughout, a green disc floret, the outermost florets of which display white stigmas and the middle flowers of which show yellow-orange anthers, red perianth lobe color and 120 mm overall flower diameter.

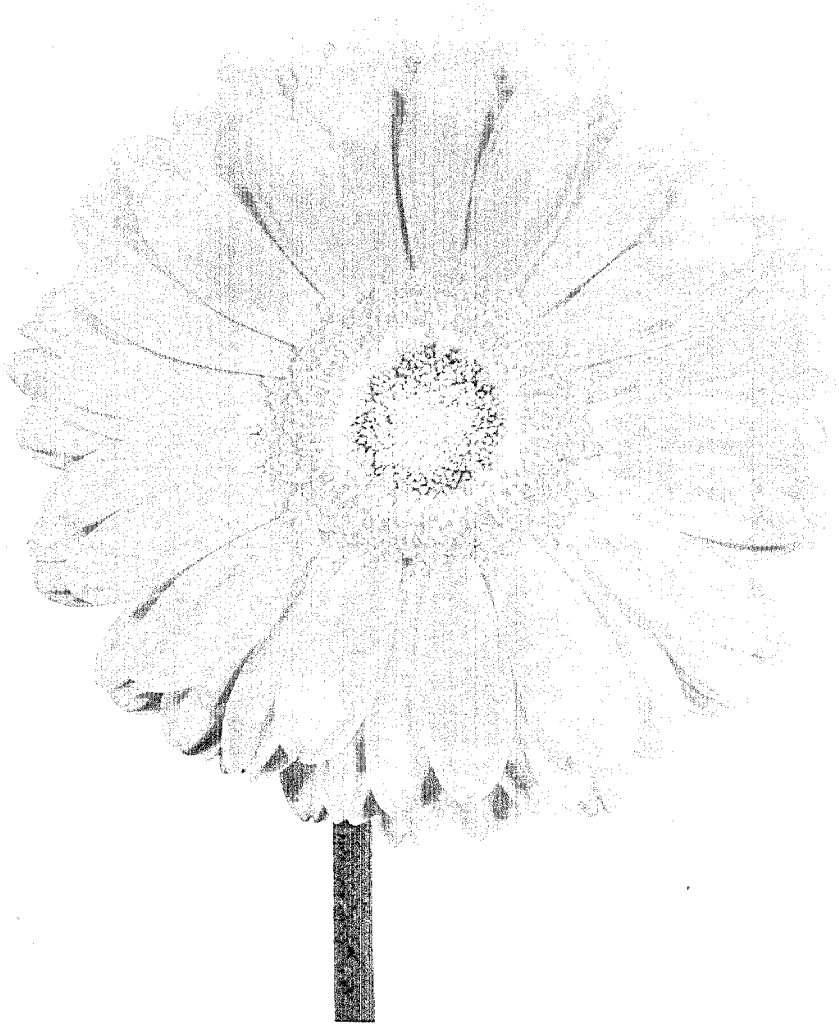

* * * * *